United States Patent [19]

Lenaghan

[11] 4,389,211

[45] Jun. 21, 1983

[54] CATAMENIAL BANDAGE

[76] Inventor: Arlene R. Lenaghan, 674 Rudgate, Bloomfield Hills, Mich. 48013

[21] Appl. No.: 269,361

[22] Filed: Jun. 1, 1981

[51] Int. Cl.³ ............................................. A61F 13/16
[52] U.S. Cl. .................................................. 604/383
[58] Field of Search ........... 128/284, 287, 288, 290 R, 128/290 W, 296; 604/378–379, 383, 385

[56] References Cited

U.S. PATENT DOCUMENTS

| | | | |
|---|---|---|---|
| 810,119 | 1/1906 | Green | 128/296 |
| 2,120,949 | 6/1938 | Hayden | 128/290 R |
| 2,508,214 | 5/1950 | Biederman | 128/296 |
| 2,869,092 | 1/1937 | Jackson, Jr. | 128/296 |
| 2,968,304 | 1/1961 | DeWeskin | 128/296 |
| 3,345,243 | 10/1967 | Kalwaites | 128/290 W |
| 3,771,525 | 11/1973 | Chapuis | 128/290 R |
| 4,022,212 | 5/1977 | Louison | 128/288 |

Primary Examiner—C. Fred Rosenbaum
Attorney, Agent, or Firm—Barnes, Kisselle, Raisch, Choate, Whittemore & Hulbert

[57] ABSTRACT

A catamenial bandage pad which is elongate in form and provided with a shell envelope of resilient material corrugated lengthwise to permit easy transverse compression but with a resilient memory to return to a laterally extended position. The shell includes absorbent filler material and a compressed element of absorbent substance which expands in the presence of liquid to respond to the quantity of liquid.

4 Claims, 9 Drawing Figures

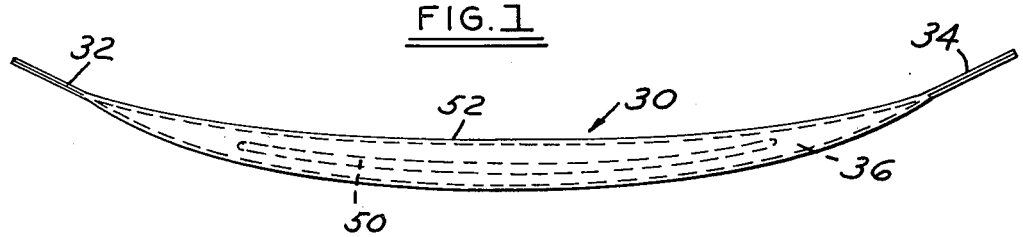
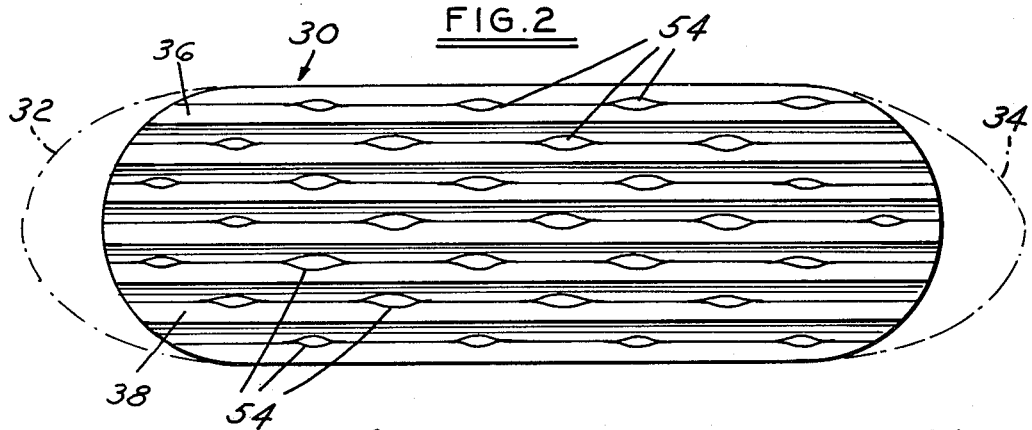
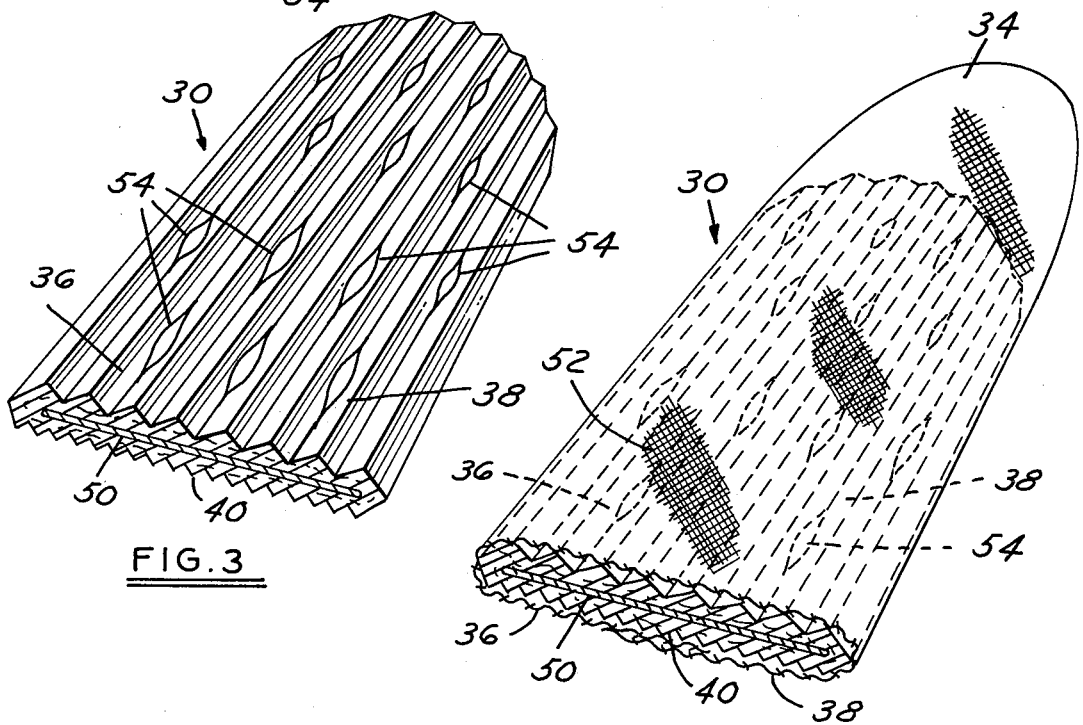
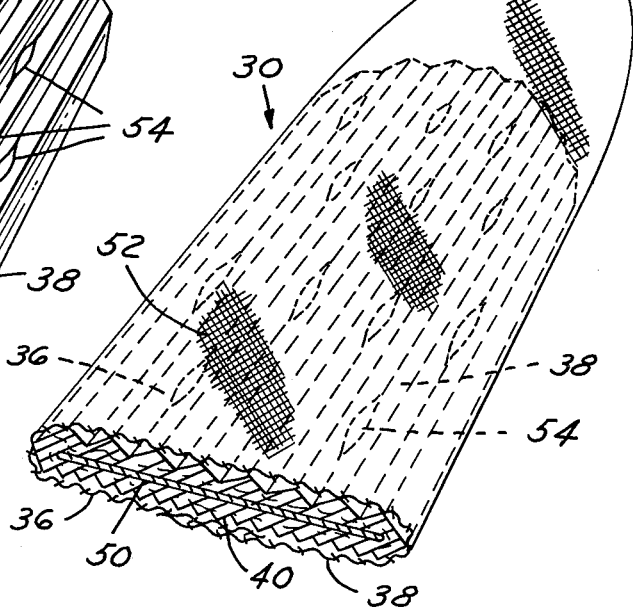
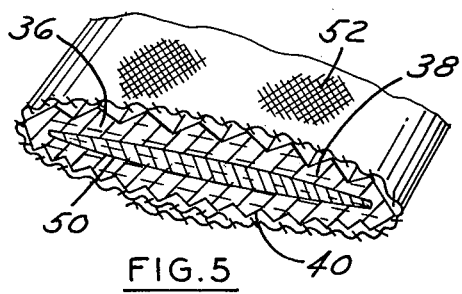

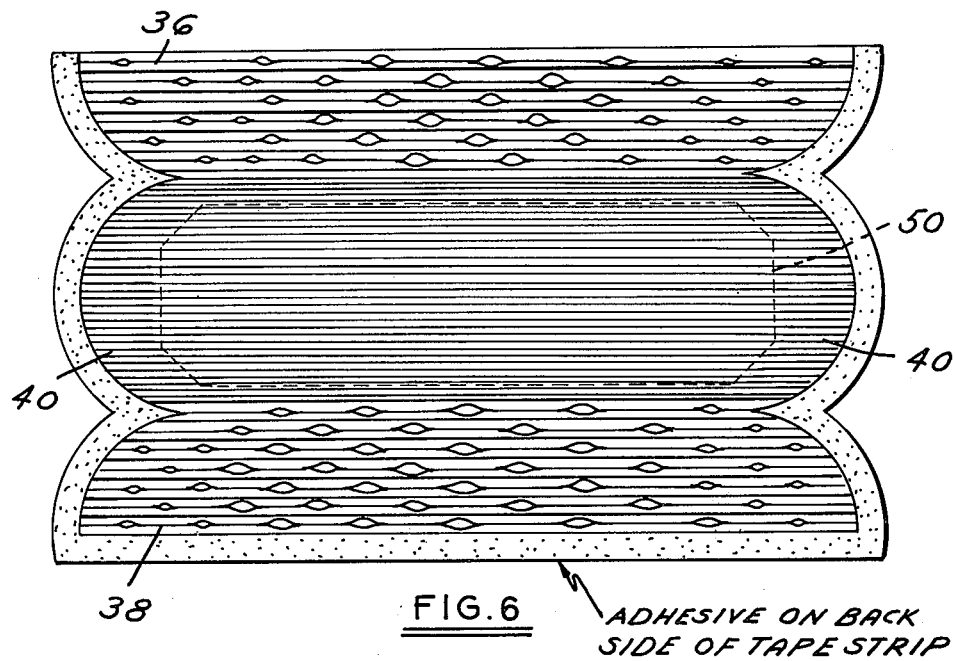
FIG. 6 — ADHESIVE ON BACK SIDE OF TAPE STRIP
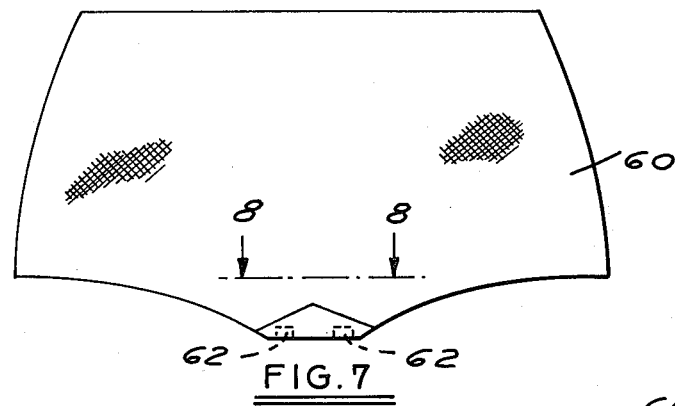
FIG. 7
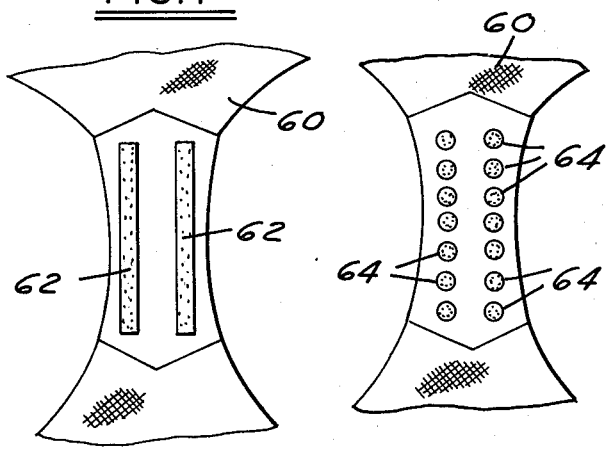
FIG. 8    FIG. 9

CATAMENIAL BANDAGE

REFERENCE TO RELATED APPLICATION

Reference is made to my copending application entitled "Catamenial Bandage", Ser. No. 269,360, filed June 1, 1981.

FIELD OF THE INVENTION

The design and manufacture of sanitary pads for use by women in the menstrual period.

BACKGROUND OF THE INVENTION

In recent months, the use of the tampon type menstrual device has been under investigation due to a toxic syndrome which has affected certain women using this type of device. This has caused a return to the more conventional sanitary pad but has resulted also in the focus of attention to the inadequacies of the usual elongate pad. These inadequacies include discomfort in use, deformation or roping which reduces the effectiveness of the absorbency, inability to adapt to variations in flow, and a resulting lack of confidence in the pad itself.

The present invention is directed to an improved type of sanitary pad which provides a more comfortable device which holds its shape and provides the necessary protection without loss of absorbency and which adapts readily to varying conditions.

Other objects and features of the invention will be apparent in the following description and claims in which the invention is described together with the manner of making and using the invention directed to persons skilled in the art.

BRIEF DESCRIPTION OF THE DRAWINGS

DRAWINGS accompany the disclosure and the various views thereof may be briefly described as:

FIG. 1, a side view of a pad constructed in accordance with the invention.

FIG. 2, a top plan view of the pad.

FIG. 3, a perspective view of the pad partially in transverse section.

FIG. 4, a perspective view of the completed pad.

FIG. 5, a sectional view of the pad showing one condition of use.

FIG. 6, a view showing the pad partially assembled.

FIG. 7, a view of a retaining panty garment.

FIG. 8, a sectional view on line 8—8 of FIG. 7.

FIG. 9, a view of a modified distribution of Velcro retainers.

DETAILED DESCRIPTION OF THE DRAWINGS

WITH REFERENCE TO THE DRAWINGS, it is an object of the invention to provide a sanitary pad which keeps its shape during its entire use but which will compress and expand transversely with body movement. The space between the upper femur portions of the body will vary with individuals and also with body position. The present pad is designed to accommodate itself to this variation. In addition, the pad contemplates the use of a hydrophillic material which is formed of compressed absorbent particles to provide a relatively thin flat pad which can expand to provide more space for absorption when in contact with fluid. Thus, the pad can be used for light menstrual flow and heavy flow, thus eliminating the use of different bulk pads.

In FIG. 1, the pad 30 is shown as arcuate in longitudinal contour with a gradual taper to relatively flat ends 32 and 34. The pad is made as illustrated in FIG. 6 of an outside shell having two wing portions 36 and 38 and a central portion 40. The shell is formed of a soft, resilient form-retaining plastic, preferably foamed, but thin and having a velvety feel such as is used in wrapping or packaging materials. It has a memory so that it will return to its original shape. The wings 36 and 38 are corrugated longitudinally as shown in FIG. 3 while the base or outside sheet is corrugated also but with finer corrugations. Thus, the lower flat section 40 is more flexible than the upper flat surface formed by wings 36, 38.

A pad 50 of compressed hydrophillic material is relatively thin and lies between the lower section 40 and the wings 36, 38. A light, filler gauze material is interposed also over and under pad 50 before the wings are folded into place with a slight overlap and heat sealed at the ends and at the seams. An envelope 52 surrounds the assembly.

The plastic sheath or shell has elongate apertures 54 in the valleys of the corrugated top 36, 38, these openings being longest and widest at the midportion of the pad and ensmalling toward the ends.

As indicated, the lower section 40 of the pad is more flexible than the top corrugated section. The compressed hydrophillic material 50 acts like a sponge, attracting the fluid from above and expanding to absorb the fluid. As this occurs, the pad 50 expands downwardly, as shown in FIG. 5, bulging the bottom wall to some degree. Thus, during days of heaviest flow, the bulkiness of the pad can be used but on the days of lighter flow, the pad will remain relatively thin. Discomfort is thus minimized in direct relation to the flow required to be absorbed.

The pad provides for the protection of the perineal portions of the body against direct contact with the largest collection of the flow in that the flow-directing valleys of the corrugations are provided with the openings 54. This, together with the attracting capabilities of the compressed absorbing material keep the flow in a constant downward movement, taking the flow beneath the ridges and away from direct contact with the perineal area. The less rigid outer wall of the pad expands as this process takes place.

The corrugated formation of the pad allows it to be compressed laterally by body movement without discomfort and it will return to its original shape when side pressure is released.

The outer covering 52 previously referenced is preferably a comfortable, hydrophobic material which is liquid permeable and will pass fluid into the pad but not retain it. This can be a soft foamed sheeting which can be heat sealed to encase the pad.

As shown in FIGS. 7 and 8, a retaining panty garment 60 may have Velcro (Trademark) strips 62 secured to the pubic area and these will cooperate with the foam outer sheath to retain the pad in place. For more flexibility, Velcro discs 64, shown in FIG. 9, can serve the same purpose as locators for the pad. Other standard means for positioning the pad can also be used.

Thus, the described pad can be smaller and flatter than the conventional sanitary pads. The corrugated material provides the necessary resistance to roping while laterally compressible to accommodate body movement. It is adaptable to the quantity of flow and can be used for either light flow days or heavy flow and is convenient to carry before use. The hydrophobic chamber provided by the outer sheath eliminates contact with the body.

What I claim is:

1. A catamenial bandage pad comprising:
(a) an elongate, relatively flat shell of resilient, form retaining material having a top and bottom surface corrugated in a longitudinal direction, the top surface having spaced openings in the valleys of the corrugations, and
(b) an elongate, relatively thin, compressed sheet of hydrophillic material encapsulated in a filler gauze and relatively coextensive with and encased in said shell, said hydrophillic material being expansible in the presence of fluid to have a sponge-like attraction for fluid entering the shell.

2. A catamenial bandage as defined in claim 1 in which the shell is surrounded by a liquid permeable but hydrophobic material.

3. A catamenial bandage as defined in claim 1 in which said shell has an elongate base portion, with side wings integral therewith, the edges of said shell having an adhesive material along the edges such that when the wings are folded together over the base portion, the edges thereof will adhere to form a closed encasement for said encapsulated hydrophillic material.

4. A catamenial bandage pad as defined in claim 1 in which the corrugated top of the shell is less resilient than the bottom of the shell.

* * * * *